United States Patent
Kuznetsov et al.

(10) Patent No.: US 10,504,759 B2
(45) Date of Patent: Dec. 10, 2019

(54) SEMICONDUCTOR METROLOGY WITH INFORMATION FROM MULTIPLE PROCESSING STEPS

(71) Applicant: KLA-Tencor Corporation, Milpitas, CA (US)

(72) Inventors: Alexander Kuznetsov, Austin, TX (US); Antonio Arion Gellineau, Santa Clara, CA (US); Andrei V. Shchegrov, Campbell, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 266 days.

(21) Appl. No.: 15/476,683

(22) Filed: Mar. 31, 2017

(65) Prior Publication Data

US 2017/0287751 A1 Oct. 5, 2017

Related U.S. Application Data

(60) Provisional application No. 62/318,166, filed on Apr. 4, 2016.

(51) Int. Cl.
*H01L 21/67* (2006.01)
*G06N 20/00* (2019.01)
(Continued)

(52) U.S. Cl.
CPC ........ *H01L 21/67253* (2013.01); *G03F 7/705* (2013.01); *G03F 7/70625* (2013.01);
(Continued)

(58) Field of Classification Search
CPC .. G03F 7/70616; G03F 7/70625; G03F 7/705; G01B 11/272; G01B 11/27;
(Continued)

(56) References Cited

U.S. PATENT DOCUMENTS 5,608,526 A 3/1997 Piwonka-Corle et al.
5,859,424 A 1/1999 Norton et al.
(Continued)

OTHER PUBLICATIONS

International Search Report dated Jul. 18, 2017, for PCT Application No. PCT/US2017/025757 filed on Apr. 3, 2017 by KLA-Tencor Corporation, 3 pages.
(Continued)

*Primary Examiner* — Elias Desta
(74) *Attorney, Agent, or Firm* — Spano Law Group; Joseph S. Spano

(57) ABSTRACT

Methods and systems for measuring process induced errors in a multiple patterning semiconductor fabrication process based on measurements of a specimen and process information from one or more previous process steps employed to fabricate the specimen are presented herein. A metrology tool is employed after a number of process steps have been executed. The metrology tool measures structural parameters of interest of metrology targets on the wafer based on measured signals and process information, and communicates correctable process parameter values to one or more process tools involved in the previous process steps. When executed by the appropriate process tool, the correctable process parameter values reduce process induced errors in the geometry of the structures fabricated by the process flow. In another aspect, multiple metrology tools are used to control a fabrication process in combination with process information from one or more process steps in the process flow.

20 Claims, 9 Drawing Sheets

(51) Int. Cl.
  *G06F 17/50* (2006.01)
  *G03F 7/20* (2006.01)
  *G01N 21/95* (2006.01)

(52) U.S. Cl.
  CPC ...... *G03F 7/70633* (2013.01); *G06F 17/5009* (2013.01); *G06N 20/00* (2019.01); *G01B 2210/56* (2013.01); *G01N 21/9501* (2013.01); *G01N 2201/12* (2013.01)

(58) Field of Classification Search
  CPC ............ H01L 22/12; G01N 2291/0289; G01N 29/06; G01N 29/46; G06F 17/5081
  See application file for complete search history.

(56) References Cited

U.S. PATENT DOCUMENTS

| | | | |
|---|---|---|---|
| 6,429,943 B1 | 8/2002 | Opsal et al. | |
| 6,633,831 B2 | 10/2003 | Nikoonahad et al. | |
| 6,734,967 B1 | 5/2004 | Piwonka-Corle et al. | |
| 6,816,570 B2 | 10/2004 | Janik et al. | |
| 6,895,075 B2 | 5/2005 | Yokhin et al. | |
| 6,972,852 B2 | 12/2005 | Opsal et al. | |
| 7,092,096 B2* | 8/2006 | Tao | H01L 22/12 250/559.24 |
| 7,478,019 B2 | 1/2009 | Zangooie et al. | |
| 7,826,071 B2 | 11/2010 | Shchegrov et al. | |
| 7,929,667 B1 | 4/2011 | Zhuang et al. | |
| 7,933,026 B2 | 4/2011 | Opsal et al. | |
| 8,142,966 B2 | 3/2012 | Izikson et al. | |
| 8,797,554 B2* | 8/2014 | Straaijer | G01B 11/24 356/625 |
| 8,843,875 B2 | 9/2014 | Pandev | |
| 2008/0144919 A1 | 6/2008 | Yedur et al. | |
| 2013/0114085 A1 | 5/2013 | Wang et al. | |
| 2013/0155406 A1 | 6/2013 | Den Boef | |
| 2014/0111791 A1 | 4/2014 | Manassen et al. | |
| 2014/0132948 A1 | 5/2014 | Shchegrov | |
| 2014/0172394 A1 | 6/2014 | Kuznetsov et al. | |
| 2014/0222380 A1 | 8/2014 | Kuznetsov et al. | |
| 2014/0297211 A1 | 10/2014 | Pandev et al. | |
| 2014/0316730 A1 | 10/2014 | Shchegrov et al. | |
| 2015/0042984 A1 | 2/2015 | Pandev et al. | |
| 2015/0046118 A1 | 2/2015 | Pandev et al. | |
| 2015/0176985 A1 | 6/2015 | Shchegrov et al. | |
| 2015/0235108 A1 | 8/2015 | Pandev | |
| 2015/0241790 A1 | 8/2015 | Pierson et al. | |
| 2015/0323471 A1 | 11/2015 | Sapiens et al. | |
| 2016/0109230 A1 | 4/2016 | Pandev et al. | |

OTHER PUBLICATIONS

Kim, Dongil, et al., "Improvement of virtual metrology performance by removing metrology noises in a training dataset," Pattern Anal Applic (2015) 18:173-189.

* cited by examiner

SEMICONDUCTOR METROLOGY WITH INFORMATION FROM MULTIPLE PROCESSING STEPS

CROSS REFERENCE TO RELATED APPLICATION

The present application for patent claims priority under 35 U.S.C. § 119 from U.S. provisional patent application Ser. No. 62/318,166, entitled "Process Information Assisted Metrology," filed Apr. 4, 2016, the subject matter of which is incorporated herein by reference in its entirety.

TECHNICAL FIELD

The described embodiments relate to metrology systems and methods, and more particularly to methods and systems for improved measurement of parameters characterizing the dimensions of structures generated by multiple patterning processes.

BACKGROUND INFORMATION

Semiconductor devices such as logic and memory devices are typically fabricated by a sequence of processing steps applied to a specimen. The various features and multiple structural levels of the semiconductor devices are formed by these processing steps. For example, lithography among others is one semiconductor fabrication process that involves generating a pattern on a semiconductor wafer. Additional examples of semiconductor fabrication processes include, but are not limited to, chemical-mechanical polishing, etch, deposition, and ion implantation. Multiple semiconductor devices may be fabricated on a single semiconductor wafer and then separated into individual semiconductor devices.

Multiple patterning techniques are now commonly employed to increase the resolution of features printed onto the semiconductor wafer for a given lithographic system. FIGS. 1A-1D depict a double patterning lithography (DPL) technique commonly referred to as a litho-etch-litho-etch (LELE) process. FIG. 1A depicts a silicon base layer 10, an interface layer 11 such as silicon dioxide, a device layer 12, a hard mask layer 13, a sacrificial layer 14, and a patterned resist layer 15 that results from a lithography patterning step. The structure of depicted in FIG. 1A is then subjected to exposure and etch steps that result in the structure illustrated in FIG. 1B. In this structure, the pattern of resist layer 15 has been effectively transferred to the hard mask layer 13. Both the sacrificial layer 14 and the patterned resist layer 15 have been removed. A number of deposition and lithographic steps are employed to arrive at the structure illustrated in FIG. 1C. FIG. 1C illustrates another sacrificial layer 16 and patterned resist layer 17 built on top of the hard mask layer 13. Patterned resist layer 17 includes a pattern having the same pitch as the first patterned resist layer 15, and also the same pitch as the pattern etched into the hard mask layer 13. However, the patterned resist layer 17 is offset from the pattern of the hard mask layer 13 by half of the pitch of the patterned resist layer 17. The structure depicted in FIG. 1C is then subjected to exposure and etch steps that result in the structure illustrated in FIG. 1D. In this structure, the pattern of resist layer 17 has been effectively transferred to the hard mask layer 13. Both the sacrificial layer 16 and the patterned resist layer 17 have been removed. FIG. 1D illustrates a pattern etched into hard mask 13 that is double the pitch of the patterned resist layers 15 and 17 generated by the mask of the lithographic system.

FIG. 1D also depicts the effects of a non-optimized DPL process. Ideally, the nominal pitch of the double patterned structure should be a constant value, P. However, due to imperfections in the DPL process, the pitch of the resulting structure may vary depending on location due to grating non-uniformities. This is commonly termed "pitch walk." A variation from the nominal pitch, P, is depicted as $\Delta P$ in FIG. 1D. In another example, a critical dimension of each resulting structure should be the same nominal value, CD. However, due to imperfections in the DPL process, a critical dimension (e.g., middle critical dimension, bottom critical dimension, etc.) of the resulting structure may vary depending on location. A variation from the desired critical dimension, CD, is depicted as $\Delta CD$ in FIG. 1D.

Pitch walk and $\Delta CD$ are exemplary geometric errors induced by imperfections in the DPL process such as misalignment between the two lithography layers, non-uniformities in the focus and exposure of the lithographic process, mask pattern errors, etc. Both pitch walk and $\Delta CD$ introduce a unit cell that is larger than expected. Although pitch walk and $\Delta CD$ are described in particular, other multiple patterning errors may be contemplated.

Although the LELE process is described with reference to FIGS. 1A-1D, many other multiple patterning processes that induce similar errors may be contemplated (e.g., litho-litho-etch, multiple litho-etch patterning, spacer defined multiple patterning, etc.). Similarly, although a double patterning process is described with reference to FIGS. 1A-1D, similar errors arise in higher order patterning processes such as quadruple patterning. Typically, errors such as pitch walk and $\Delta CD$ are more pronounced in structures that result from higher order patterning processes.

Metrology processes are used at various steps during a semiconductor manufacturing process to detect defects on wafers to promote higher yield. Optical metrology techniques offer the potential for high throughput measurement without the risk of sample destruction. A number of optical metrology based techniques including scatterometry and reflectometry implementations and associated analysis algorithms are commonly used to characterize critical dimensions, film thicknesses, composition and other parameters of nanoscale structures.

A common approach to control a semiconductor fabrication process is to employ a metrology tool after each critical process step in the fabrication process. In general, as critical steps are more densely sampled, process control is improved. However, inserting a metrology step after each process step is expensive, both in fabrication time and expense. As the number of critical process steps has increased for advanced technology nodes, the insertion of a metrology step after each critical process step has become cost prohibitive. Moreover, with each metrology node the number of critical process steps that can be measured in a cost effective manner compared to the total number of critical process steps is decreasing.

As metrology steps are eliminated in the process flow for advanced technology nodes, such as a LELE multiple patterning process, metrology results become ineffective for purposes of process control for all of the intervening process steps. For example, in a LELE multiple patterning process, a metrology step may be only performed after the last process step. The results of this measurement may be effectively used to correct the last process step, but not earlier process steps. This limitation exists even if multiple metrology steps are employed. The last process step before metrology may be effectively corrected, but current metrology does not provide sufficient measurement information to correct all other process steps.

Metrology applications involving the measurement of structures generated by multiple process steps, and multiple patterning processes, in particular, present challenges due to practical limitations on the number of metrology insertion points. Increasingly small resolution requirements, multi-parameter correlation, increasingly complex geometric structures, and increasing use of opaque materials complicate this problem, and leave undesirable gaps in the control of advanced fabrication processes. Thus, methods and systems for improved process control of advanced fabrication processes are desired.

SUMMARY

Methods and systems for measuring process induced errors in a multiple patterning semiconductor fabrication process based on measurements of a specimen and process information from one or more previous process steps employed to fabricate the specimen are presented herein. Based on measured errors, corrected process parameter values are communicated to the appropriate process tool to improve process performance. In this manner, a metrology tool provides corrections to one or more process tools employed to perform any of the preceding process steps.

The metrology system receives process information from any of the process tools employed to perform any of the preceding process steps. Process tools include lithography tools, etch tools, deposition tools, chemical mechanical planarization (CMP) tools, etc. Process information received by the metrology tool includes, but in not limited to, process control parameters, process tool set-up parameters, process environment parameters, process data collected from sensors on board a process tool, metrology data collected from sensors on board a process tool, etc.

In one aspect, a metrology tool is employed at a metrology step after a number of process steps have been executed. The metrology tool measures structural parameters of interest of metrology targets on the wafer in physical state and communicates correctable process parameter values to one or more process tools involved in one or more of the previous process steps. When executed by the appropriate process tool, the correctable process parameter values reduce process induced errors in the geometry of the structures fabricated by the process flow.

In another aspect, multiple metrology tools are used to control a fabrication process in combination with process information from one or more process steps in the process flow. In addition to process information, metrology information from an additional metrology step inserted into the process flow is also employed to improve the metrology of the structure and to improve process control.

In some embodiments, a metrology tool employs a physically based measurement model to estimate the values of structural parameters of interest from measurement data (e.g., measured spectra) and process information.

In some other embodiments, a metrology tool employs an input-output measurement model to estimate the values of structural parameters of interest from measurement data (e.g., measured spectra) and process information. These models include signal response metrology models, neural network models, support vector machines models, etc.

In another further aspect, a signal response metrology (SRM) measurement model is trained on measurement signals and associated process information from multiple targets integrated into one multi-target set and operates on measurement signals from the same multiple targets. This approach de-correlates critical parameters from each other and from other process variations.

In some embodiments, assist targets are located next to the primary measurement target and are subject to the same process variations. In these embodiments, the training set of metrology targets includes a primary, nominally dimensioned target and one or more assist targets that have different nominal values of the parameters of interest.

The foregoing is a summary and thus contains, by necessity, simplifications, generalizations and omissions of detail; consequently, those skilled in the art will appreciate that the summary is illustrative only and is not limiting in any way. Other aspects, inventive features, and advantages of the devices and/or processes described herein will become apparent in the non-limiting detailed description set forth herein.

DETAILED DESCRIPTION

Reference will now be made in detail to background examples and some embodiments of the invention, examples of which are illustrated in the accompanying drawings.

Methods and systems for measuring process induced errors after multiple steps in a multiple patterning semiconductor fabrication process based in part on process information from one or more of the multiple steps are presented herein. Based on the measured errors, corrected process parameter values are communicated to the appropriate process tool to improve process performance. In this manner, the metrology tool provides corrections not only to the process tool employed to perform the last process step before measurement by the metrology tool, but to one or more process tools employed to perform any of the preceding process steps.

The metrology system receives process information from any of the process tools employed to perform any of the preceding process steps. Process tools include lithography tools, etch tools, deposition tools, chemical mechanical planarization (CMP) tools, etc. Process information received by the metrology tool includes, but in not limited to, process control parameters, process tool set-up parameters, process environment parameters, process data collected from sensors on board a process tool, metrology data collected from sensors on board a process tool, etc. In some examples, a process tool includes integrated metrology sensors to measure process information that is communicated to the metrology tool. For example, a lithography tool may include an optical reflectometer to measure wafer geometry. In another example, an etch tool may include an optical emission spectroscopy sensor to monitor and control a plasma source of the etch tool. These sensors alone are not sufficient to supply information to enable full metrology of a device structure. However, the inventors have discovered that these signals combined with metrology signals generated by a metrology tool enable metrology and process control of multi-step fabrication processes that would otherwise be uncontrolled.

Figure 1A:
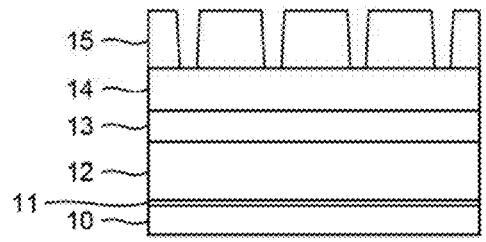
FIGS. 1A-1D depict selected steps of a double patterning lithography (DPL) technique commonly referred to as a litho-etch-litho-etch (LELE) process.
Figure 1B:
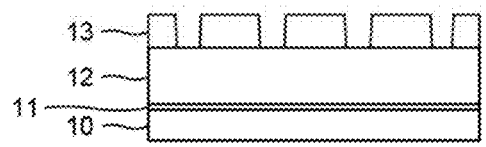
Figure 1C:
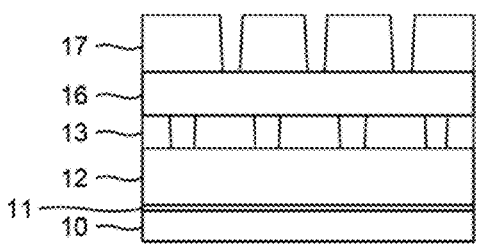
Figure 1D:
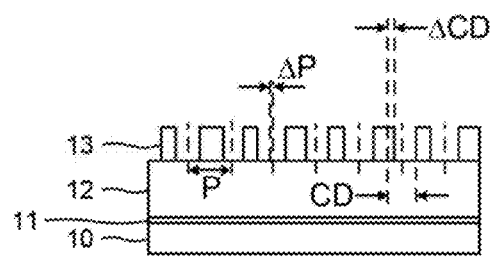
Figure 2:
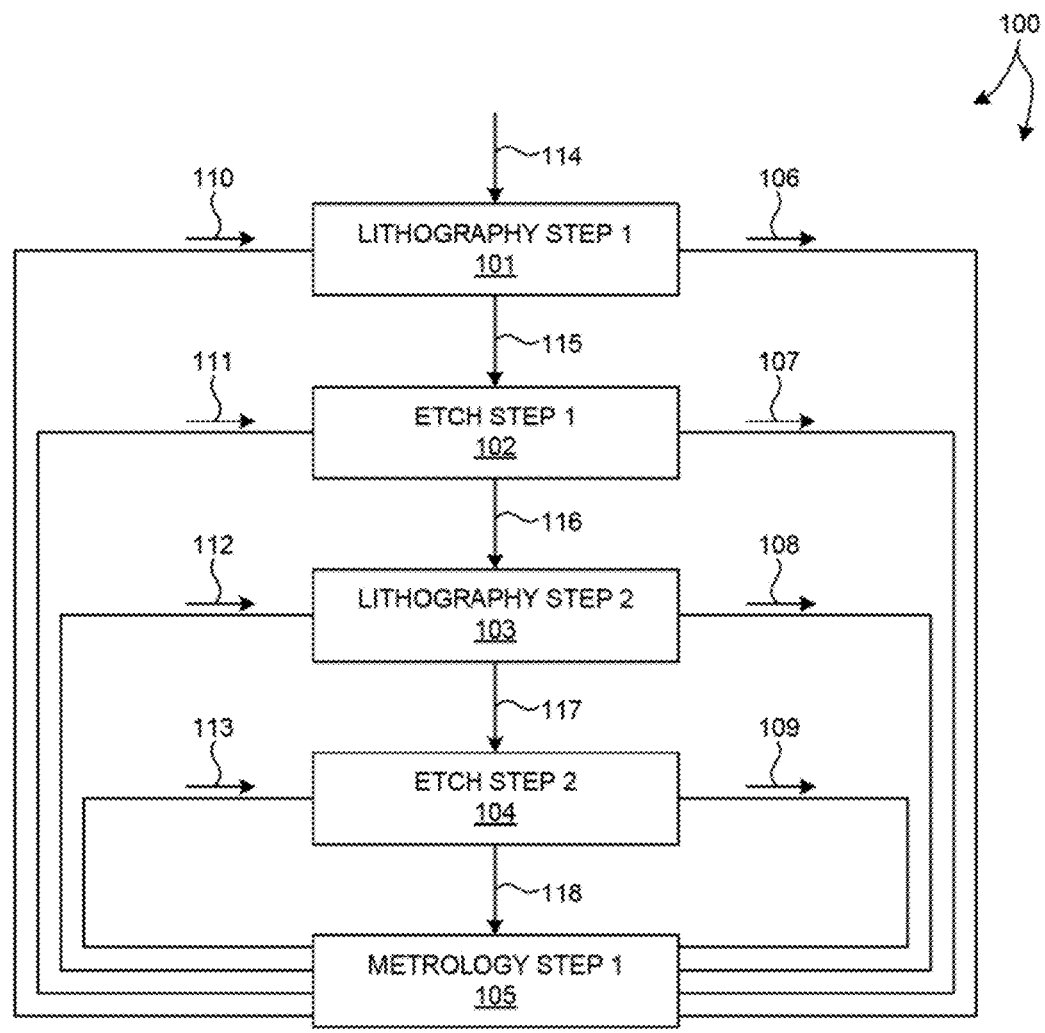
FIG. 2 depicts a fabrication process flow 100 that includes a sequence of fabrication process steps and a single metrology step.

FIG. 2 depicts a fabrication process flow 100 that includes a sequence of fabrication process steps including a lithography step 101, an etch step 102, another lithography step 103, another etch step 104, and finally a metrology step 105. An incoming wafer in a particular physical state 114 within the fabrication process is transformed by lithography step 101 to a different physical state 115 as a result of the lithography process. Similarly, etch step 102 transforms the wafer from state 115 to state 116, lithography step 103 transforms the wafer from state 116 to state 117, etch step 104 transforms the wafer from state 117 to state 118.

In one aspect, a metrology tool is employed at metrology step 105 to measure structural parameters of interest of metrology targets on the wafer in physical state 118 and to communicate correctable process parameter values to one or more process tools involved in one or more of process steps 101-104. When executed by the appropriate process tool, the correctable process parameter values reduce process induced errors in the geometry of the structures fabricated by process flow 100.

As depicted in FIG. 2, process information 106 is communicated from a lithography tool employed to execute lithography step 101 to the metrology tool employed to execute metrology step 105. Similarly, process information 107 is communicated from an etch tool employed to execute etch step 102 to the metrology tool, process information 108 is communicated from a lithography tool employed to execute lithography step 103 to the metrology tool, and process information 109 is communicated from an etch tool employed to execute etch step 104 to the metrology tool.

Although, as depicted in FIG. 2, process information from each process step of process flow 100 is communicated to the metrology tool, in general, process information from any one or more of the process steps may be communicated to the metrology tool.

As depicted in FIG. 2, the metrology tool generates correctable process parameter values based on the values of one or more structural parameters of the wafer in state 118 measured by the metrology tool at metrology step 105 and the received process information (e.g., any of process information 106-109). For example, as depicted in FIG. 2, correctable process parameter values 110 are communicated to the lithography tool employed to execute lithography step 101. Similarly, correctable process parameter values 111 are communicated to an etch tool employed to execute etch step 102, correctable process parameter values 112 are communicated to the lithography tool employed to execute lithography step 103, and correctable process parameter values 113 are communicated to an etch tool employed to execute etch step 104.

Although, as depicted in FIG. 2, correctable process parameter values are communicated to a tool executing each process step of process flow 100, in general, correctable process parameter values may be communicated to a tool executing any one or more of the process steps.

Figure 3:
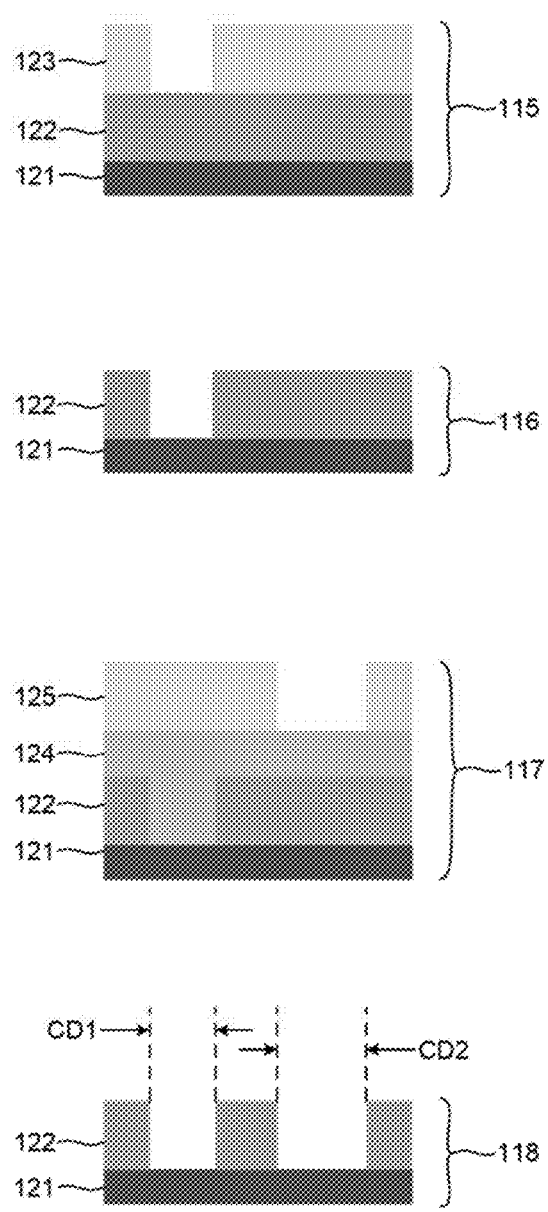
FIG. 3 depicts an example of trench formation generated by a particular example of process flow 100 depicted in FIG. 2.

FIG. 3 depicts an example of trench formation generated by a particular example of process flow 100 depicted in FIG. 2. FIG. 3 depicts a metrology target at each state of trench formation within lithography-etch, lithography-etch (LELE) process flow 100. At physical state 115 (after lithography step 101), the structure of interest includes a base layer 121, a device layer 122, and a patterned resist layer 123. At physical state 116 (after etch step 102), the patterned resist layer 123 is completely removed, along with a portion of device layer 122 exposed to light during lithography step 101. At this point, the first trench feature of the device layer is formed. At physical state 117, a sacrificial layer 124, and another patterned resist layer 125 are added during lithography step 103. At physical state 118, the patterned resist layer 125, the sacrificial layer 124, and another portion of device layer 122 are removed by etch step 104. At this point, the second trench feature of the device layer is formed, and the resulting structure is measured by a metrology tool at metrology step 105.

In this example, the metrology tool is able to measure a critical dimension associated with each trench feature, CD1 and CD2. However, without additional process information the metrology system is not able to determine which trench feature was produced by which lithography step. In this example, dosage information 106 is communicated from the lithography tool employed to execute lithography step 101 to the metrology tool executing metrology step 105. In addition, dosage information 108 is communicated from the lithography tool employed to execute lithography step 103 to the metrology tool. Based on the received dosage information, the metrology tool associates the each trench with the corresponding lithography step that produced the particular trench. In this example, a larger dosage at lithography step 101 (i.e., Dose1>Dose2) causes a larger critical dimension (i.e., CD1>CD2). In this manner, the first trench, having dimension CD1, is associated with lithography step 101 and the second trench, having dimension CD2 is associated with lithography step 103.

In a further aspect, the metrology tool generates and communicates a correctable process parameter value 110 to the lithography tool executing lithography step 101 to correct the dimension of trench 1. Similarly, the metrology tool generates and communicates a correctable process parameter value 112 to the lithography tool executing lithography step 103 to correct the dimension of trench 2.

In some examples, the metrology tool is able to perform measurements of structural parameters of interest. For example, in some embodiments the metrology tool is able to independently measure CD1 and CD2 as described with reference to FIG. 2. However, in some other examples, the metrology tool is unable to independently measure all of the parameters of interest. Quite often a metrology tool is capable of measuring average trench size (i.e., (CD1+CD2)/2) because the measured signals are mostly sensitive to changes in volume, rather than position. In these examples, process information received by the metrology tool enables a measurement of both CD1 and CD2, independently. In this manner, process information in combination with metrology signal information enables improved metrology capability in addition to improved process control.

FIG. 2 depicts a LELE, or (LE)$^2$, fabrication process flow. However, in general, the methods and systems described herein may be applied to any multiple patterning process flow such as a (LE)$^N$ fabrication process flow that involves N litho-etch steps, where N is any positive integer number, any self-aligned multiple patterning technique, etc.

In another aspect, multiple metrology tools are used to control a fabrication process in combination with process information from one or more process steps in the process flow. In addition to process information described with reference to FIG. 2, metrology information from any additional metrology step inserted into the process flow is also employed to improve the metrology of the structure and to improve process control.

Figure 4:
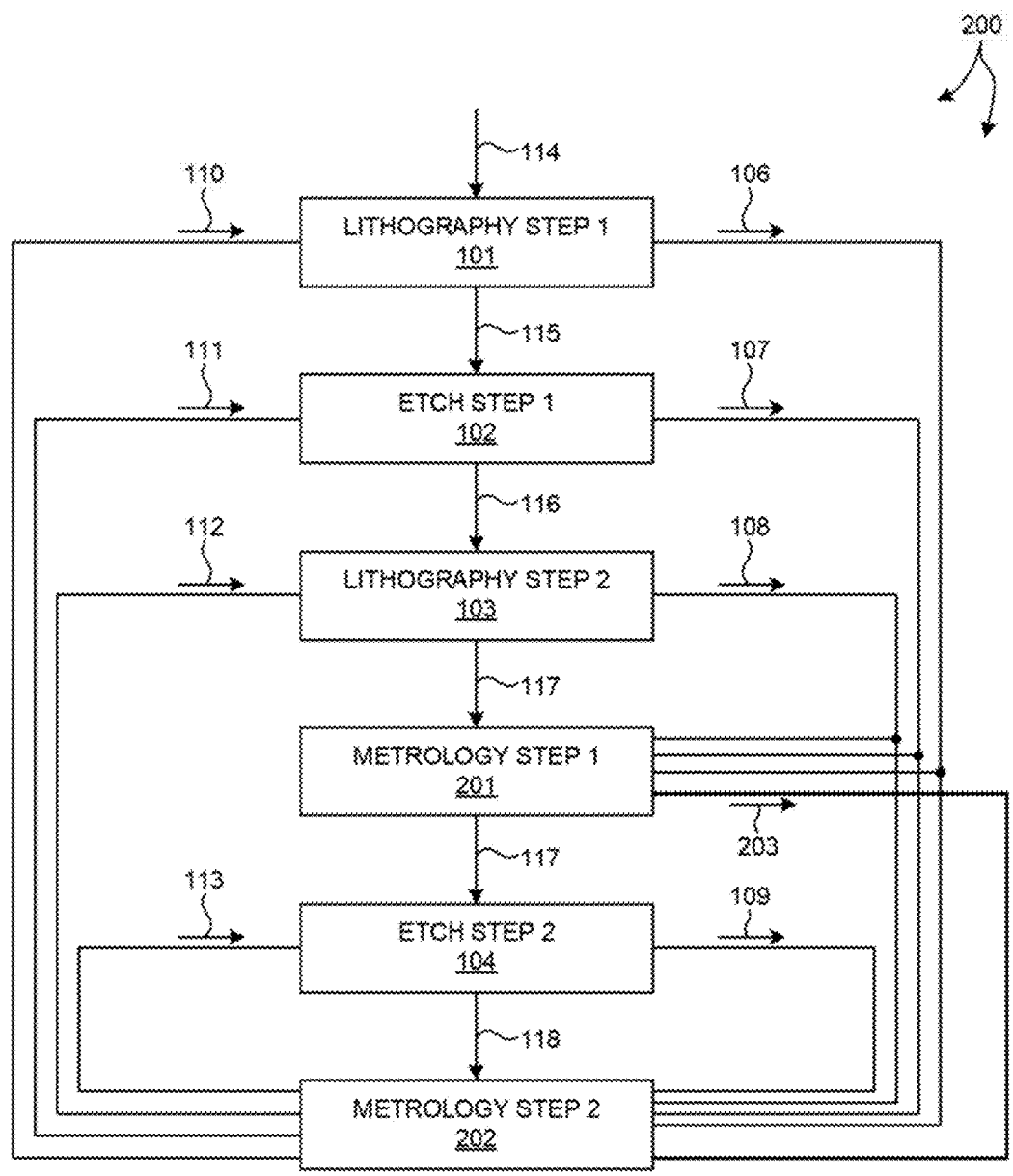
FIG. 4 depicts a fabrication process flow 200 that includes a sequence of fabrication process steps and two metrology steps.

FIG. 4 depicts a fabrication process flow 200 that includes a sequence of fabrication process steps and two metrology steps. Like numbered elements are analogous to those described with reference to FIG. 2. As depicted in FIG. 4, process flow 200 includes lithography steps 101 and 103, and etch steps 102 and 104, as described with reference to FIG. 2. However, in addition, process flow 200 includes two metrology steps. Metrology step 201 is inserted in the middle of process flow 200 and metrology step 202 is performed at the end of process flow 200.

In one aspect, the wafer at physical state 117 is measured by a metrology tool executing metrology step 201, and an indication of these measurement results is communicated to a metrology tool executing metrology step 202 at the end of the process flow 200. In turn, at metrology step 202, a metrology tool is employed to measure structural parameters of interest of metrology targets on the wafer in physical state 118 based on process information received from any of the previous process steps (i.e., steps 101-104) and the measurement results 203 received from the intermediate metrology step 201.

As described with reference to FIG. 2, the metrology tool executing metrology step 202 generates correctable process parameter values for one or more of the process steps of process flow 200 based on the measurement results obtained at metrology step 202. The correctable process parameter values are communicated to one for more process tools involved in one or more of process steps 101-104. When executed by the appropriate process tool, the correctable process parameter values reduce process induced errors in the geometry of the structures fabricated by process flow 200.

FIGS. 2-4 depict examples of (LE)$^N$ type multiple patterning processes. However, in addition, the metrology and process control techniques described herein are applicable to self-aligned multiple patterning processes. Advanced process nodes (e.g., 5 nanometer and 3.5 nanometer process nodes) require complex patterning schemes to achieve desired fin pitches. For example, to achieve a fin pitch below 20 nanometers, a self-aligned octuplet patterning (SAOP) process may be required.

Figure 5:
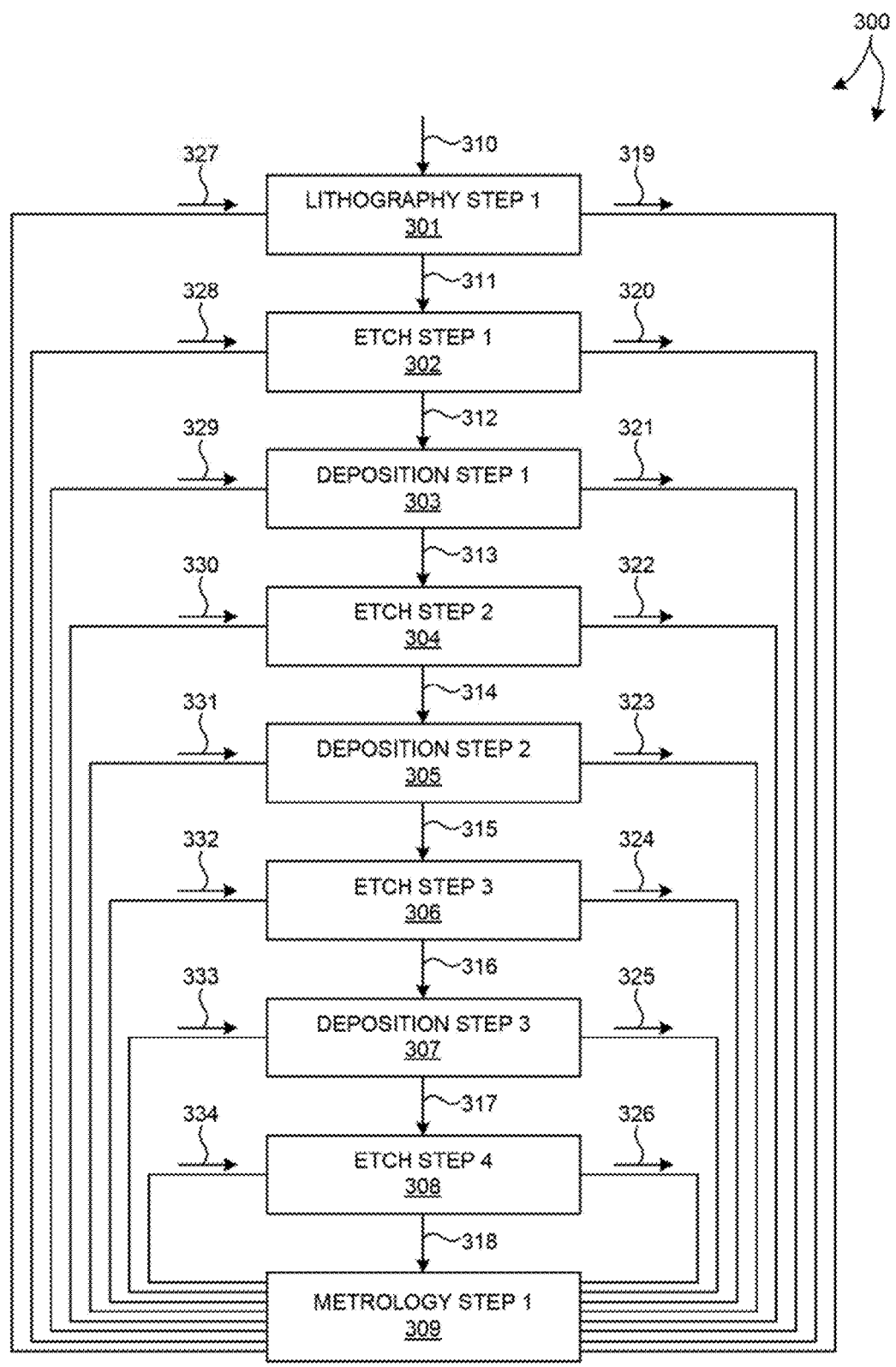
FIG. 5 depicts a process flow 300 exemplary of a self-aligned octuplet patterning process.

FIG. 5 depicts a process flow 300 exemplary of a SAOP process. Process flow 300 includes a lithography step followed by a repeating sequence of etch and deposition steps. As depicted in FIG. 5, an incoming wafer in a particular physical state 310 within the fabrication process is transformed by lithography step 301 to a different physical state 311 as a result of the lithography process. Similarly, etch step 302 transforms the wafer from state 311 to state 312, deposition step 303 transforms the wafer from state 312 to state 313, etch step 304 transforms the wafer from state 313 to state 314, deposition step 305 transforms the wafer from state 314 to state 315, etch step 306 transforms the wafer from state 315 to state 316, deposition step 307 transforms the wafer from state 316 to state 317, etch step 308 transforms the wafer from state 317 to state 318.

In one aspect, a metrology tool is employed at metrology step 309 to measure structural parameters of interest of metrology targets on the wafer in physical state 318 and communicate correctable process parameter values to one or more process tools involved in one or more of process steps 301-308. When executed by the appropriate process tool, the correctable process parameter values reduce process induced errors in the geometry of the structures fabricated by process flow 300.

As depicted in FIG. 5, process information 319 is communicated from a lithography tool employed to execute lithography step 301 to the metrology tool employed to execute metrology step 309. Similarly, process information 320 is communicated from an etch tool employed to execute etch step 302 to the metrology tool, process information 321 is communicated from a deposition tool employed to execute deposition step 303 to the metrology tool, process information 322 is communicated from an etch tool employed to execute etch step 304 to the metrology tool, process information 323 is communicated from a deposition tool employed to execute deposition step 305 to the metrology tool, process information 324 is communicated from an etch tool employed to execute etch step 306 to the metrology tool, process information 325 is communicated from a deposition tool employed to execute deposition step 307 to the metrology tool, and process information 326 is communicated from an etch tool employed to execute etch step 308 to the metrology tool.

Although, as depicted in FIG. 5, process information from each process step of process flow 300 is communicated to the metrology tool, in general, process information from any one or more of the process steps may be communicated to the metrology tool.

As depicted in FIG. 5, the metrology tool generates correctable process parameter values based on the values of one or more structural parameters of the wafer in state 318 measured by the metrology tool at metrology step 309 and the received process information (e.g., any of process information 319-326). For example, as depicted in FIG. 5, correctable process parameter values 327 are communicated to the lithography tool employed to execute lithography step 301. Similarly, correctable process parameter values 328 are communicated to an etch tool employed to execute etch step 302, correctable process parameter values 329 are communicated to the deposition tool employed to execute deposition step 303, correctable process parameter values 330 are communicated to an etch tool employed to execute etch step 304, correctable process parameter values 331 are communicated to the deposition tool employed to execute deposition step 305, correctable process parameter values 332 are communicated to an etch tool employed to execute etch step 306, correctable process parameter values 333 are communicated to the deposition tool employed to execute deposition step 307, and correctable process parameter values 334 are communicated to an etch tool employed to execute etch step 308.

Although, as depicted in FIG. 5, correctable process parameter values are communicated to a tool executing each process step of process flow 300, in general, correctable process parameter values may be communicated to a tool executing any one or more of the process steps.

Figure 6:
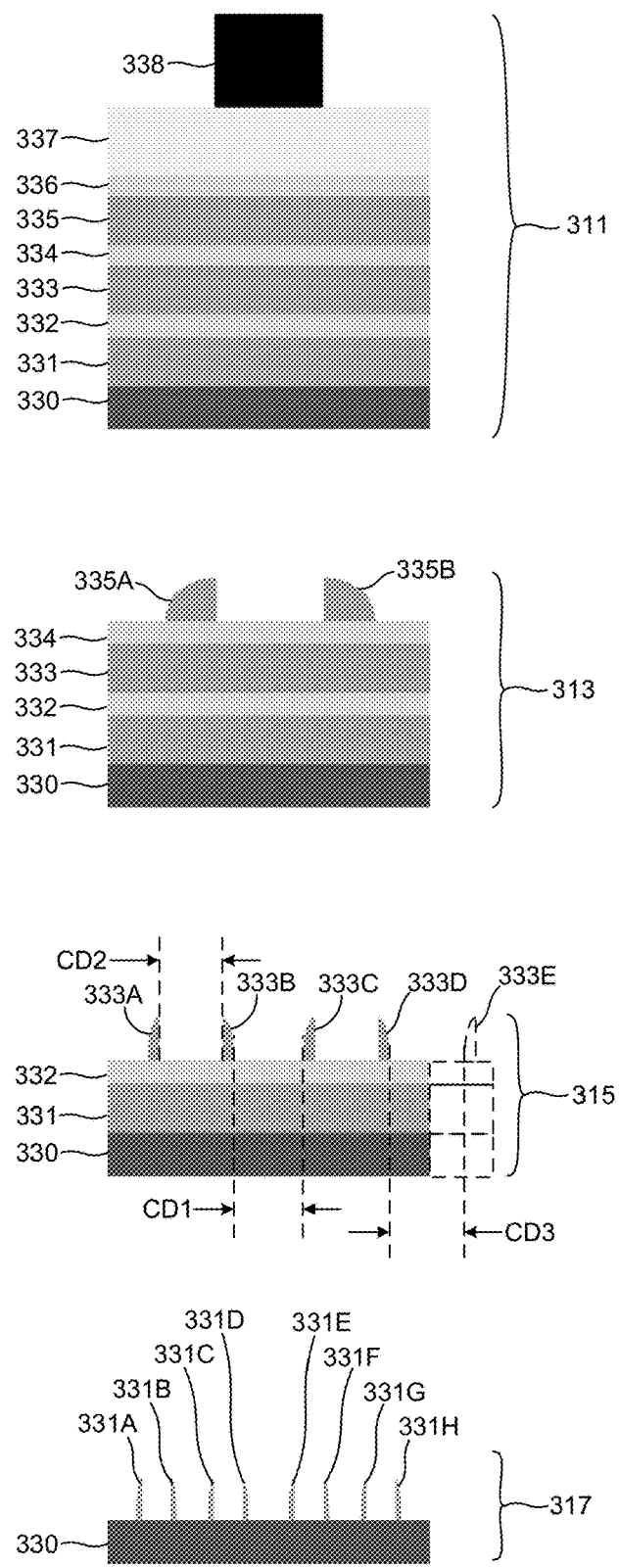
FIG. 6 depicts an example of fin spacer formation generated by a particular example of process flow 300 depicted in FIG. 5.

FIG. 6 depicts an example of fin spacer formation generated by a particular example of process flow 300 depicted in FIG. 5. FIG. 6 depicts a metrology target at each state of fin spacer formation within SAOP process flow 300. At physical state 311 (after lithography step 301), the structure of interest includes a substrate layer 330, and a repeating sequence of nitride layers 331, 333, 335 and oxide layers 332, 334, and 336, a bottom anti-reflective coating (BARC) layer 337, and a patterned resist layer 338. At physical state 313 (after deposition step 303), the patterned resist layer 123 and BARC layer 337 are completely removed, along with a portion of nitride layer 335, leaving behind two spacer structures 335A-B. At this point, the first set of fin spacer structures is formed. At physical state 315, layers 334 and 335 are removed, along with a portion of nitride layer 333, leaving behind four spacer structures 333A-D. At this point, the second set of fin spacer structures is formed. At physical state 317, layers 332 and 333 are removed, along with a portion of nitride layer 331, leaving behind eight spacer structures 331A-H. At this point, the third set of fin spacer structures is formed, and the resulting structure is measured by a metrology tool at metrology step 309.

In this example, the metrology tool is not able to directly measure a critical dimension associated with each fin spacer feature 331A-H. However, with additional process information the metrology system is able to determine the dimensions of each fin spacer feature and which fin spacer features are sensitive to each process step. In this example, dosage information 319 is communicated from the lithography tool employed to execute lithography step 301 to the metrology tool, along with an indication 321 of the spacer critical dimension, CD1, an indication 323 of the spacer critical dimension, CD2, and an indication 325 of the spacer critical dimension, CD3. Based on the received dosage and dimension information, the metrology tool associates each fin spacer with the corresponding process steps that produced the particular fin spacer feature. In this manner, augmenting metrology with process information enables control of the SAOP process with a single metrology tool.

In some embodiments, a metrology tool employs a physically based measurement model to estimate the values of structural parameters of interest from measurement data (e.g., measured spectra). Metrology techniques employing physical, model based measurements typically require a parameterized, geometric model of the patterned structure. Exemplary parameters include critical dimension, pitch walk, or other parameters of interest. In addition, an accurate electromagnetic model of the interaction between the optical system and the structure under measurement is required to simulate signals generated during measurement. Nonlinear regression of simulated signals against measured signals is applied to determine parameters of the modeled structure. This approach requires accurate modeling of the structure and the material properties.

In these embodiments, process information received from tools employed to execute previous process steps is fed directly into the measurement model. In some examples, process parameter values of the measurement model are fixed to values received from the process tools. In other examples, received process information is further processed to arrive at particular values of model parameters, or mathematical relationships among model parameters. In this manner, the received process information is employed to constrain the measurement model and reduce parameter correlations.

In some other embodiments, a metrology tool employs an input-output measurement model to estimate the values of structural parameters of interest from measurement data (e.g., measured spectra). These models include signal response metrology models, neural network models, support vector machines models, etc.

In a further aspect, a trained input-output measurement model is employed to estimate values of structural parameters of interest based on measured signals and process information received from tools employed to fabricate the sample under measurement at previous process steps. The combination of measurement signals and process information contains more information required to separate and measure critical features than would otherwise be achievable based on either measurement signals or process information alone.

In some examples a SRM measurement model is created based on process information from previous process steps (e.g., simulated process data or actual process data associated with the fabrication of a Design of Experiments (DOE) wafer) and raw measurement data (e.g., simulated spectra or spectra collected from the DOE wafer) collected from measurement sites including multiple pattern metrology targets (simulated or actual). Machine learning, feature extraction, and other techniques are employed to build a direct input-output model (i.e., transfer function) that relates DOE process information and spectra of one or more multiple patterned targets and corresponding reference measurements of the parameter of interest. In some embodiments, the training set of multiple patterned metrology targets includes targets that are nominally the same, i.e., the targets vary from one another because of process variations. In some embodiments, the process variations that impact the parameters of interest are intentionally amplified for purposes of model training.

Figure 7:
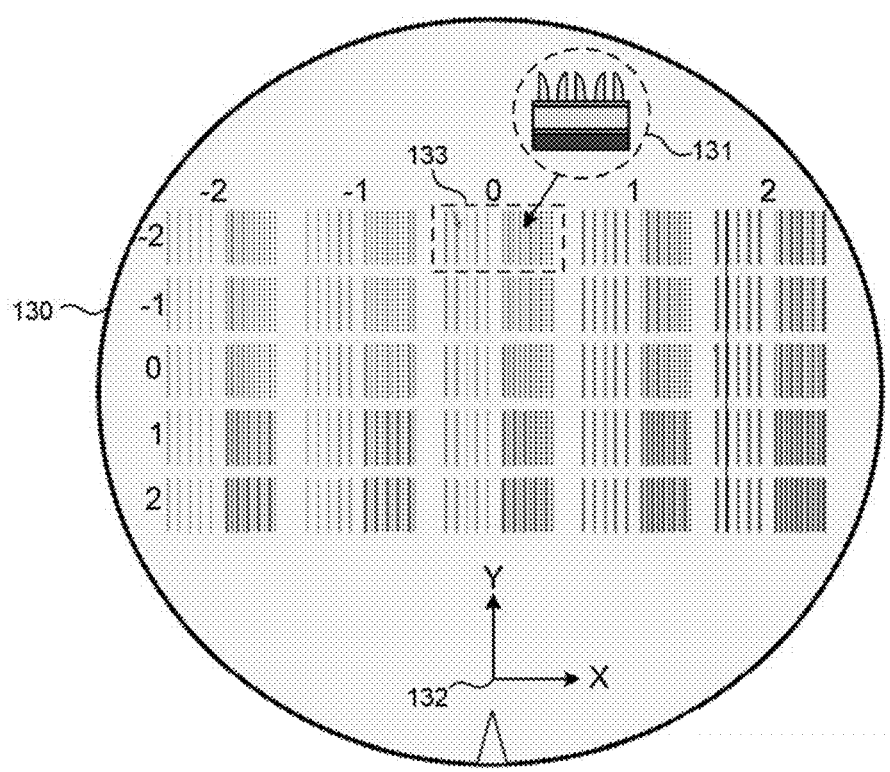
FIG. 7 depicts a semiconductor wafer 130 having a number of metrology targets located at various measurement sites over the surface of the wafer.

In one example, the transfer function relates process information and scatterometry signals with corresponding CD-SEM measurements of a SAQP target 131 depicted in FIG. 7. An SRM model is created for each parameter of interest, and the same model is used to perform subsequent measurements on other measurement sites.

To train the SRM model, an amount of raw measurement data associated with measurements of a plurality of measurement sites and corresponding process information from previous process steps is received by a computing system (e.g., computing system 330). Each of the plurality of measurement sites includes a multiple patterned metrology target characterized by at least one parameter of interest generated by at least two patterning steps of a multiple patterning process. A value of the parameter(s) of interest is known at each of the plurality of measurement sites.

For purposes of model training, measurement data may be acquired from any location with known perturbations in the design parameters, e.g., structure or process parameters. These locations, for example, may be in the scribe line, on-device, or may be at other locations on the wafer where, for example, lithographic exposure conditions or reticle design characteristics vary over a range of values. In another example, measurement data may be acquired from different device locations (e.g., a location with dense features and a location with isolated features, or locations with two different CDs on mask). In general, the measurement data is acquired from different locations that are perturbed in a known way. The perturbation may be known from mask data, Equipment Data Acquisition (EDA) data, process data, etc.

In one example, any of focus, exposure, and overlay are varied systematically across the device or the wafer. In another example, a randomized Focus and Exposure Matrix (FEM) is employed to reduce correlation with underlayer parameters as described in U.S. Pat. No. 8,142,966 to Izikson et al., the entirety of which is incorporated herein by reference.

In a preferred embodiment, the set of systematic variations is implemented in the fabrication of an actual DOE wafer. The DOE wafer is subsequently measured to generate the raw measurement data. A manufactured wafer includes systematic errors which cannot be easily modeled by simulation. For example, the effect of underlayers is more accurately captured by measurements of a real wafer. The underlayer contribution can be decorrelated from the measurement responses by modifying process parameters during manufacture, e.g., focus and exposure variations, for a fixed underlayer condition. In another example, the underlayer contribution can be mitigated by taking multiple data sets from features with varying top layer topography and constant underlayer conditions. In one example, the top layer may include a periodic structure and the underlayer may be non-periodic.

Measurement locations may be selected to increase measurement sensitivity. In one example, measurements performed at line ends are most sensitive to changes in focus. In general, measurements should be taken at structures that are most sensitive to changes in the parameter to be measured.

Although it is preferred to perform actual measurements of DOE wafers, in some other examples the process information and measurement response of a DOE wafer for different, known structural parameter values may be simulated. In these examples, the process information and raw measurement data is synthetically generated. For example, a process simulator such as the Positive Resist Optical Lithography (PROLITH) simulation software available from KLA-Tencor Corporation, Milpitas, Calif. (USA) may be employed. In general, any process modeling technique or tool may be contemplated within the scope of this patent document (e.g., Coventor simulation software available from Coventor, Inc., Cary, N.C., USA).

In some examples, the raw measurement data includes two ellipsometric parameters ($\Psi$, $\Delta$) over a spectral range obtained at different measurement sites. However, in general, the measurement data may be any measurement data indicative of the structural or geometric properties of the structures patterned onto the surface of a semiconductor wafer.

In some examples, the measurement data is associated with simulations of process parameters and corresponding measurements of the measurement sites on the surface of a DOE wafer (e.g., wafer 130). For example, the measurement data may include simulated spectral measurements associated with the multiple pattern metrology target associated with each measurement site.

In some other examples, the measurement data is associated with actual measurements of the measurement sites on the surface of a DOE wafer (e.g., wafer 130). The measurement data includes actual spectral measurements associated with the multiple pattern metrology target associated with each measurement site.

In some examples, the measurement data is associated with measurements of the plurality of measurement sites on a Design of Experiments (DOE) wafer and the parameter(s) of interest characterizing the multiple patterned metrology target is measured by a reference measurement system at each of the measurement sites. The reference metrology system is a trusted metrology system such as a Scanning Electron Microscope (SEM), Tunneling electron Microscope (TEM), Atomic Force Microscope (AFM), or an x-ray measurement system such as a Small-Angle X-Ray Scatterometer (SAXS) or an X-Ray Fluorescence (XRF) system that is able to accurately measure the parameter value. However, typically, the reference metrology system generally lacks the capability to operate as an inline metrology system, for example, due to low throughput, high measurement uncertainty for the measurement of individual sites, etc.

In some embodiments, process variations and corresponding parameter variations are organized in a Design of Experiments (DOE) pattern on the surface of a semiconductor wafer (e.g., DOE wafer), for example, as described herein with reference to FIG. 7. In this manner, the measurement system interrogates different locations on the wafer surface that correspond with different process and corresponding structural parameter values. In the example described with reference to FIG. 7, the measurement data is associated with a DOE wafer processed with known variations in CD1 and CD2 depicted in FIG. 6. For example, CD1 is varied by changing dose during lithography, and CD2 is varied by changing thickness of spacers 335A-B. CD3 is the distance between spacer 333D and the spacer 333E associated with the adjacent unit cell (illustrated with dashed lines, rather than shading). CD3 is related to CD1 and CD2 by equation (1), $$CD3 = \text{LithoPitch} - 4T_{spacer} - CD_1 - 2CD_2 \qquad (1)$$

where LithoPitch is a predefined pitch of the resist grating pattern and Tspacer is the thickness of spacers 333A-D. Although, in this example, dose and spacer thickness are varied to produce the desired parameter variations, in general, measurement data associated with any known variation of process parameters (e.g., lithography focus, exposure, and other local or global parameters), structural parameter, or both, may be contemplated.

FIG. 7 depicts a semiconductor wafer 130 having a number of die (e.g., die 133) located at various measurement sites over the surface of the wafer. In the embodiment depicted in FIG. 7, the die is located at measurement sites arranged in a rectangular grid pattern in alignment with the depicted x and y coordinate frame 132. Each die includes a SAQP metrology target 131. In the embodiment depicted in FIG. 7, each multiple patterned metrology target 131 includes a set of lines that result from a first patterning step along with at least one more set of interposed lines that result from a subsequent step in the multiple patterning process. As a result, each multiple patterned metrology target includes a grating structure having a repeated pattern of spacer structures such as multiple patterned unit cell 131. The geometry of multiple patterned unit cell 131 is characterized by CD1, CD2, CD3, and pitchwalk as described with reference to FIG. 6.

Wafer 130 includes an array of die having different, known structural parameter values. Thus, CD1 has different, known values depending on its location on the wafer 130. In this manner, wafer 130 can be considered a Design of Experiments (DOE) wafer. It is desirable for the DOE wafer to include a matrix of multiple patterned metrology targets that span the full range of structural parameter values (e.g., CD1) that are expected to arise from the underlying process window. As depicted in FIG. 7, the values of CD1 change for different columns of die (columns index in the x-direction). In this manner, wafer 130 includes columns of die that include different values of CD1 depending on their location on the wafer. Moreover, the values of CD1 range over the values of CD1 that are expected to arise from the process window.

In some embodiments a set of DOE wafers similar to DOE wafer 130 are fabricated with each DOE wafer of the set having a different, known nominal value of CD2. CD2 is varied by changing spacer thickness or etch conditions, which affect the entire wafer. Thus, each DOE wafer is fabricated under slightly different process conditions to yield different nominal values of CD2. Each DOE wafer of the set includes a range of different, known values of CD1 as described hereinbefore with reference to wafer 130.

In some examples, one or more features of the raw measurement data is extracted by reducing a dimension of the measurement data. Although, this reduction is optional, when it is employed, the SRM measurement model is determined based at least in part on the one or more extracted features. Similarly one or more features of the process information received from previous process steps is extracted by reducing a dimension of the process information.

In general, the dimension of the measurement data, process information, or both, may be reduced by a number of known methods, including a principal components analysis, a non-linear principal components analysis, a selection of individual signals from the second amount of measurement data, and a filtering of the second amount of measurement data.

In some examples, the measurement data, process information, or both, is analyzed using Principal Components Analysis (PCA), non-linear PCA, kernel PCA, Independent Component Analysis (ICA), Fast Fourier Transform analysis (FFT), Discrete Cosine Transform analysis (DCT), or a combination of these techniques to extract features that most strongly reflect the variations in process parameter, structural parameters, or both, that are present at the different measurement sites. In some other examples, a signal filtering technique may be applied to extract signal data that most strongly reflects the parameter variations present at the different measurement sites. In some other examples, individual signals that most strongly reflect the parameter variations present at the different measurement sites may be selected from multiple signals present in the measurement data. Although, it is preferred to extract features from the measurement data and process information to reduce the dimension of data subject to subsequent analysis, it is not strictly necessary.

An SRM measurement model is determined based on process information and associated raw measurement signals, or reduced versions of one or both. A trained SRM measurement model is structured to receive measurement data generated by a metrology system at one or more measurement sites and associated process information from previous process steps, and directly determine structural parameter values associated with each measurement target. In a preferred embodiment, the SRM measurement model is implemented as a neural network model. In one example, the number of nodes of the neural network is selected based on the features extracted from the measurement data, process information, or both. In other examples, the SRM measurement model may be implemented as a linear model, a polynomial model, a response surface model, a decision tree model, a random forest model, a support vector machine model or other types of models.

The SRM measurement model is trained based on the known values of the parameter of interest. In some examples, the trained SRM measurement model is generated using DOE process information, raw measurement data, and known parameter values. The model is trained such that its output fits the defined expected response for all the spectra in the process variation space defined by the DOE spectra.

In some examples, the trained SRM model is used to calculate structure parameter values directly from measured data (e.g., spectra) collected from actual device structures of other wafers (e.g., product wafers) and associated process information from previous processes employed to fabricate the measured structures. The SRM measurement model receives measurement data (e.g., measured spectra) and associated process information directly as input and provides parameter values as output, and is thus, a trained input-output model.

Additional details related to model generation, training, and utilization as part of the measurement process are described in U.S. Pat. No. 8,843,875 to Pandev, U.S. Patent Publication No. 2014/0297211 by Pandev et al., U.S. Patent Publication No. 2014/0316730 by Shchegrov et al., U.S. Patent Publication No. 2014/0172394, U.S. Patent Publication No. 2015/0042984 by Pandev et al., U.S. Patent Publication No. 2015/0046118 by Pandev et al., U.S. Patent Publication No. 2015/0235108 by Pandev, U.S. Patent Publication No. 2016/0109230 by Pandev et al., and U.S. Patent Publication No. 2015/0323471 by Sapiens et al., the entirety of each are incorporated herein by reference.

In some examples, an amount of optical measurement data associated with measurements of a metrology target on a surface of a semiconductor wafer and process information associated with previous process steps employed to fabricate the metrology target are received by a computing system (e.g., computing system 330). The parameter(s) of interest is indicative of a geometric error induced by the multiple patterning process.

In one example, structural parameters CD1, CD2, CD3, and pitchwalk of the target structure depicted in FIG. 6 are parameters of interest. These parameters are provided by way of non-limiting example. In general, many other structural parameters (e.g., sidewall angle, bottom critical dimension, etc.) may be employed to indicate geometric errors induced by a multiple patterning process.

In some embodiments, a product wafer under measurement includes an array of nominally valued structures. Thus, CD1, CD2, CD3, and pitchwalk have the same nominal values regardless of location on the wafer.

In some examples, the measurement data includes two ellipsometric parameters ($\Psi$, $\Delta$) over a spectral range obtained at different measurement sites. The measurement data includes spectral measurements associated with the multiple patterned metrology target associated with each measurement site. Although, in some examples, the measurement data is spectral measurement data, in general, the measurement data may be any measurement data indicative of the structural or geometric properties of the structures patterned onto the surface of a semiconductor wafer.

The value of at least one parameter of interest associated with the metrology target is determined based on the measurement data, associated process information, and a trained SRM measurement model. The value of the parameter of interest is indicative of a geometric error induced by the multiple patterning process. The value of the parameter of interest is calculated directly from the trained SRM measurement model.

The value of the parameter of interest is stored in a memory (e.g., memory 332).

Due to structural symmetry present in some targets, critical dimensions often cannot be directly measured from scatterometry signals derived from an individual target and associated process information alone. For example, the scatterometry signals from a grating structure having a positive valued perturbation in critical dimension, CD, (e.g., CD+x) are identical to the scatterometry signals from a grating structure having a negative valued perturbation in CD (e.g., CD−x).

In one further aspect, a SRM measurement model is trained on measurement signals and associated process information from multiple targets integrated into one multi-target set and operates on measurement signals from the same multiple targets. This approach de-correlates critical parameters from each other and from other process variations.

In some embodiments, assist targets are located next to the primary measurement target and are subject to the same process variations (e.g., SAQP process variations). In these embodiments, the training set of metrology targets includes a primary, nominally dimensioned target and one or more assist targets that have different nominal values of the parameters of interest.

The assist targets are formed during the lithography process steps. In some examples, a mask with different line to space ratio and/or different pitch can be used to create assist targets. It is preferable to locate the primary and assist targets as close together as possible to enhance the accuracy of the SRM measurement model. In some embodiments, both primary and assist metrology targets are located adjacent to one another at each measurement site. By locating the metrology targets close together, simplifying assumptions used to link parameters of both metrology targets are less likely to induce significant errors. For example, the thickness of an underlying layer is very likely to be the same value for both metrology targets as long as the targets are located in close proximity. Thus, for adjacent metrology targets, the thickness of the underlying layer can be treated as the same constant value without inducing significant error.

The use of assist targets to train and use a SRM measurement model is analogous to the single target approach described hereinbefore. However, in addition the training of the multi-target SRM measurement model requires training data from the assist targets and the primary metrology target. Similarly, the use of the multi-target SRM measurement model requires measurement data from the assist targets and the primary measurement target. It is noted however, that reference measurement data for training need only be collected from the primary target as the specific parameter values associated with the assist targets is not of interest.

In some embodiments, a SRM measurement model is trained and used based on measurement signals from a metrology target measured at multiple steps of the multiple patterning process. Measured spectra or measured parameters of interest from one or more previous process steps are fed forward for training and use of the SRM measurement model associated with the primary target. This approach also de-correlates critical parameters from each other and from other process variations.

This approach does not require the extra wafer space needed to implement additional assist targets. However, this approach does require that wafer measurements be performed at multiple process steps.

The use of measurement data collected at multiple process steps to train and use a SRM measurement model is analogous to the single target approach described hereinbefore. However, in addition, the training of the SRM measurement model requires measurement of the primary target at a minimum of two different process steps. Similarly, the use of the SRM measurement model requires measurement data from the primary target at the different process steps. It is noted, however, that reference measurement data for training need only be collected from the primary target at the latest process step as only the specific parameter values of the target at this step are of interest.

As described herein, reference measurements obtained using other technologies are required to train the SRM model. CD-SEM is an exemplary measurement technique that is known for its high measurement uncertainty.

Specific examples involving LELE and SAOP are described herein by way of non-limiting example. In general the methods and systems described herein may be employed to improve measurement of parameters of interest generated by any multiple patterning technique (e.g., self-aligned double, triple, quadruple, octuple patterning, double litho, double etch (LELE) patterning, etc.).

Figure 8:
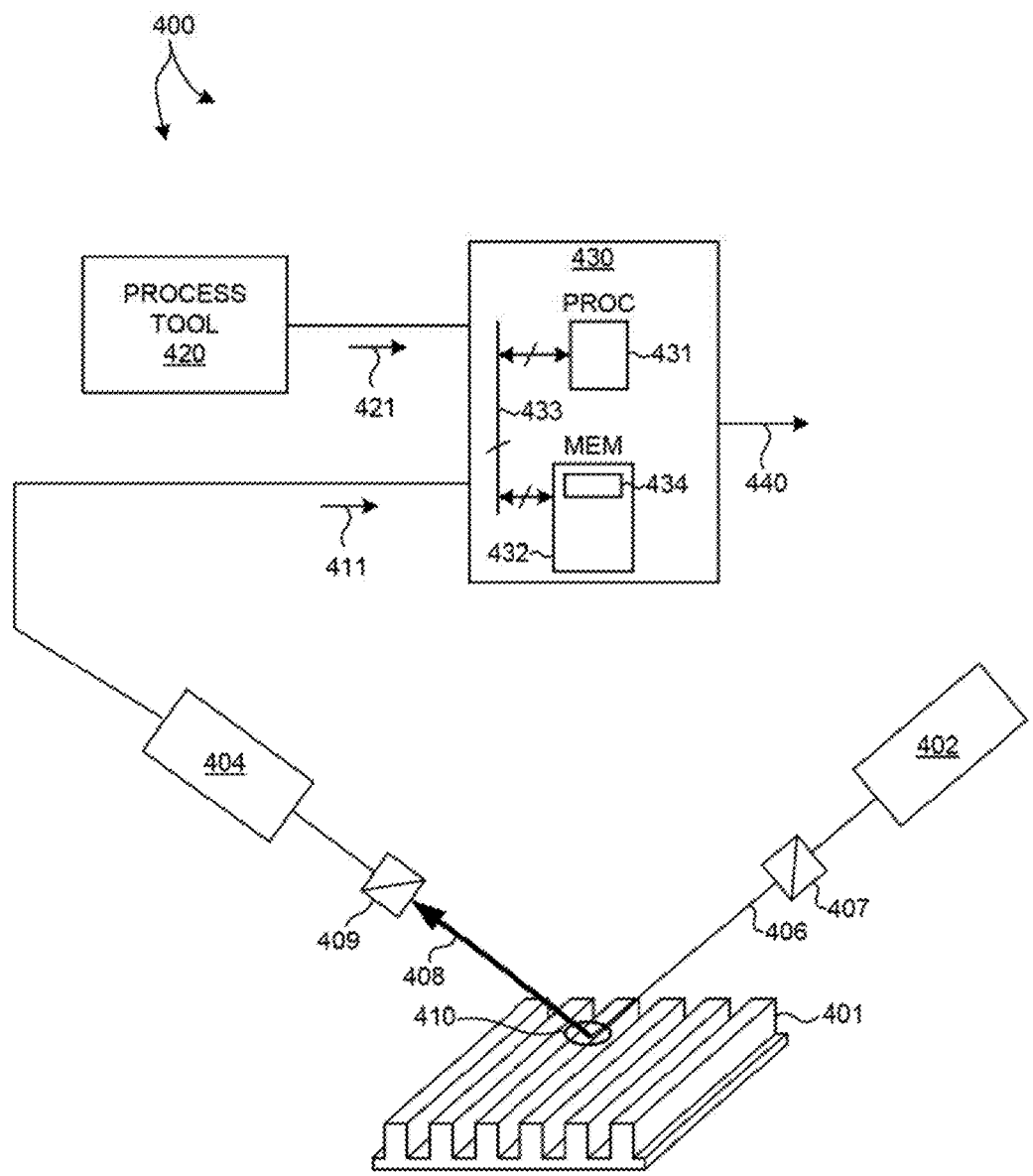
FIG. 8 illustrates a system 500 for measuring characteristics of a specimen in accordance with the exemplary methods presented herein.

FIG. 8 illustrates a system 400 for measuring characteristics of a specimen in accordance with the exemplary methods presented herein. As shown in FIG. 8, the system 400 may be used to perform spectroscopic ellipsometry measurements of one or more structures 410 of a specimen 401. In this aspect, the system 400 may include a spectroscopic ellipsometer equipped with an illuminator 402 and a spectrometer 404. The illuminator 402 of the system 400 is configured to generate and direct illumination of a selected wavelength range (e.g., 150-2000 nm) to the structure disposed on the surface of the specimen 401. In turn, the spectrometer 404 is configured to receive illumination reflected from the surface of the specimen 401. It is further noted that the light emerging from the illuminator 402 is polarized using a polarization state generator 407 to produce a polarized illumination beam 406. The radiation reflected by the structure disposed on the specimen 401 is passed through a polarization state analyzer 409 and to the spectrometer 404. The radiation received by the spectrometer 404 in the collection beam 408 is analyzed with regard to polarization state, allowing for spectral analysis by the spectrometer of radiation passed by the analyzer. These spectra 411 are passed to the computing system 430 for analysis of the structure.

As depicted in FIG. 8, system 400 includes a single measurement technology (i.e., SE). However, in general, system 400 may include any number of different measurement technologies. By way of non-limiting example, system 400 may be configured as a spectroscopic ellipsometer (including Mueller matrix ellipsometry), a spectroscopic reflectometer, a spectroscopic scatterometer, an overlay scatterometer, an angular resolved beam profile reflectometer, a polarization resolved beam profile reflectometer, a beam profile reflectometer, a beam profile ellipsometer, any single or multiple wavelength ellipsometer, or any combination thereof. Furthermore, in general, measurement data collected by different measurement technologies and analyzed in accordance with the methods described herein may be collected from multiple tools, rather than one tool integrating multiple technologies.

In a further embodiment, system 400 may include one or more computing systems 430 employed to perform measurements based on measured spectra and process information with as described herein. The one or more computing systems 430 may be communicatively coupled to the spectrometer 404. In one aspect, the one or more computing systems 430 are configured to receive measurement data 411 associated with measurements of the structure of specimen 401. The one or more computing systems 430 may also be communicatively coupled to one or more process tools 420 configured to execute a previous process step employed to fabricate sample 401 under measurement. In one aspect, the one or more computing systems 430 are configured to receive process information 421 associated with any of the previous process steps, measurements of the structure of specimen 401 at any of the previous process steps, or a combination thereof.

It should be recognized that the various steps described throughout the present disclosure may be carried out by a single computer system 430 or, alternatively, a multiple computer system 430. Moreover, different subsystems of the system 400, such as the spectroscopic ellipsometer 404, may include a computer system suitable for carrying out at least a portion of the steps described herein. Therefore, the aforementioned description should not be interpreted as a limitation on the present invention but merely an illustration. Further, the one or more computing systems 430 may be configured to perform any other step(s) of any of the method embodiments described herein.

In addition, the computer system 430 may be communicatively coupled to the spectrometer 404 in any manner known in the art. For example, the one or more computing systems 430 may be coupled to computing systems associated with the spectrometer 404. In another example, the spectrometer 404 may be controlled directly by a single computer system coupled to computer system 430.

The computer system 430 of the metrology system 400 may be configured to receive and/or acquire data or information from the subsystems of the system (e.g., spectrometer 404 and the like) or the one or more process tools 420 by a transmission medium that may include wireline and/or wireless portions. In this manner, the transmission medium may serve as a data link between the computer system 430 and other systems or subsystems of the system 400.

Computer system 430 of the metrology system 400 may be configured to receive and/or acquire data or information (e.g., measurement results, modeling inputs, modeling results, etc.) from other systems by a transmission medium that may include wireline and/or wireless portions. In this manner, the transmission medium may serve as a data link between the computer system 430 and other systems (e.g., memory on-board metrology system 400, external memory, process tools 420, a reference measurement source, or other external systems). For example, the computing system 430 may be configured to receive measurement data from a storage medium (i.e., memory 432 or an external memory) via a data link. For instance, spectral results obtained using spectrometer 404 may be stored in a permanent or semi-permanent memory device (e.g., memory 432 or an external memory). In this regard, the spectral results may be imported from on-board memory or from an external memory system. Moreover, the computer system 430 may send data to other systems via a transmission medium. For instance, a measurement model or a structural parameter value 440 determined by computer system 430 may be communicated and stored in an external memory. In this regard, measurement results may be exported to another system.

Computing system 430 may include, but is not limited to, a personal computer system, mainframe computer system, workstation, image computer, parallel processor, or any other device known in the art. In general, the term "computing system" may be broadly defined to encompass any device having one or more processors, which execute instructions from a memory medium.

Program instructions 434 implementing methods such as those described herein may be transmitted over a transmission medium such as a wire, cable, or wireless transmission link. For example, as illustrated in FIG. 8, program instructions 434 stored in memory 432 are transmitted to processor 431 over bus 433. Program instructions 434 are stored in a computer readable medium (e.g., memory 432). Exemplary computer-readable media include read-only memory, a random access memory, a magnetic or optical disk, or a magnetic tape.

In some embodiments, the illumination light and light collected from the illuminated measurement site includes multiple, different wavelengths. In some embodiments, the light is collected from the illuminated measurement site at multiple, different collection angles. By detecting light at multiple wavelengths and angles of collection, measurement sensitivity to pitch walk and variation in critical dimensions (e.g., CD) is improved. In some embodiments, the light is collected from the illuminated measurement site at multiple, different azimuthal angles. These out-of-plane measurements may also improve measurement sensitivity to pitch walk and variations in critical dimensions. In some embodiments, the collection of optical measurement data is optimized for a particular set of system settings, e.g., spectroscopic or angular resolved system, one or more azimuth angles one or more wavelengths, and any combination thereof.

Figure 9:
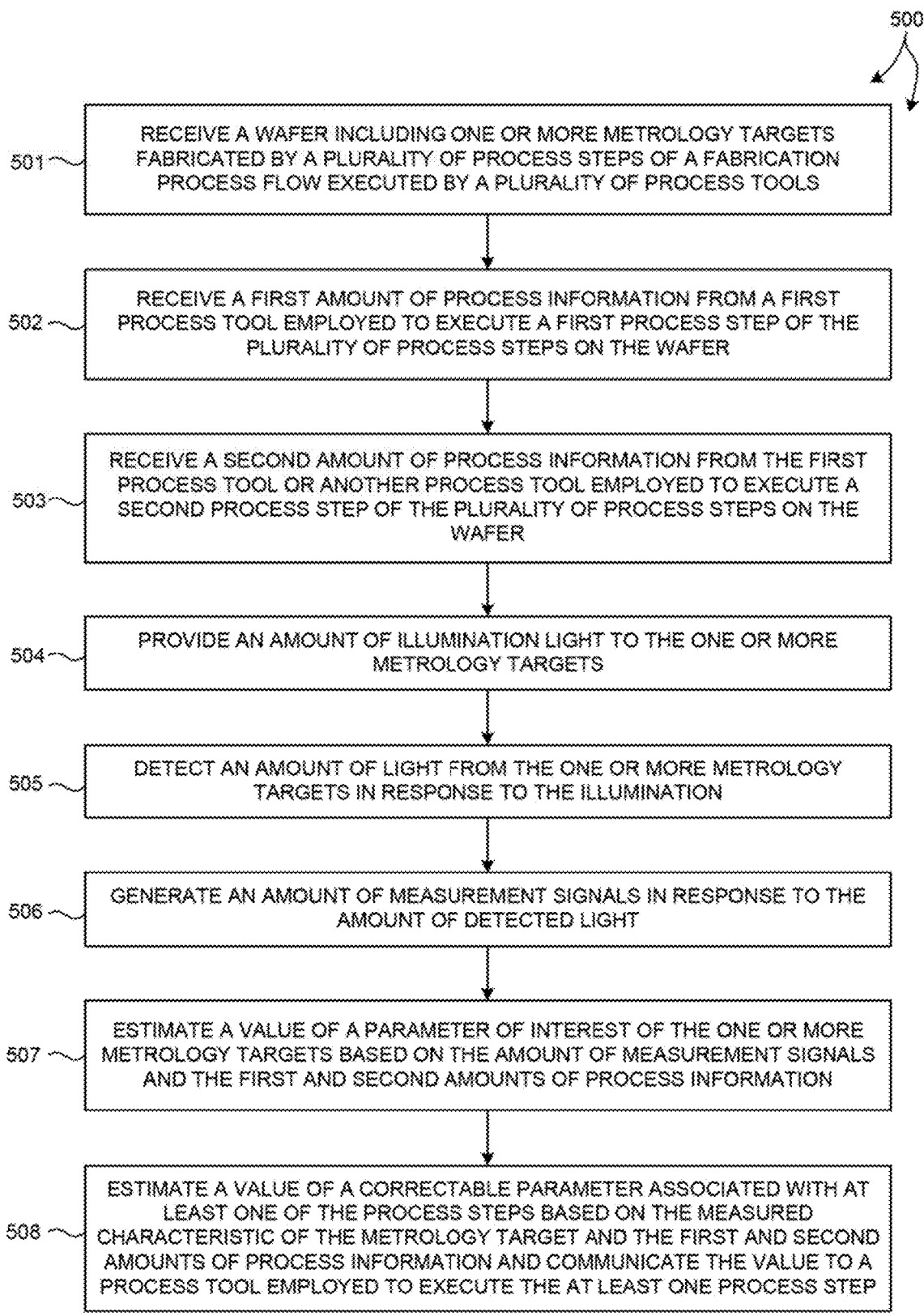
FIG. 9 is a flowchart illustrative of a method 500 of determining one or more parameter values characterizing geometric errors induced by a multiple patterning process based on measurements and process information.

FIG. 9 illustrates a method 500 suitable for implementation by a metrology system such as metrology system 400 illustrated in FIG. 8 of the present invention. In one aspect, it is recognized that data processing blocks of method 500 may be carried out via a pre-programmed algorithm executed by one or more processors of computing system 430, or any other general purpose computing system. It is recognized herein that the particular structural aspects of metrology system 400 do not represent limitations and should be interpreted as illustrative only.

In block 501, a wafer is received by a metrology system (e.g., metrology system 400). The wafer includes one or more metrology targets fabricated by a plurality of process steps of a fabrication process flow executed by a plurality of process tools.

In block 502, a first amount of process information is received onto a computing system of the metrology system from a first process tool employed to execute a first process step of the plurality of process steps on the wafer.

In block 503, a second amount of process information is received onto the computing system of the metrology system from the first process tool or another process tool employed to execute a second process step of the plurality of process steps on the wafer.

In block 504, an amount of illumination light is provided to the one or more metrology targets by an illumination subsystem of the metrology system.

In block 505, an amount of light from the one or more metrology targets in response to the illumination is detected by a detector subsystem of the metrology system.

In block 506, measurement signals are generated by the detector subsystem in response to the amount of detected light.

In block 507, a value of a parameter of interest of the one or more metrology targets is estimated based on the measurement signals and the first and second amounts of process information.

In block 508, a value of a correctable parameter associated with at least one of the process steps is estimated based on the measured characteristic of the metrology target and the first and second amounts of process information. In addition, the value of the correctable parameter is communicated a process tool employed to execute the at least one process step.

In some examples, the use of measurement data associated with multiple targets for model building, training, and measurement eliminates, or significantly reduces, the effect of under layers in the measurement result. In one example, measurement signals from two targets are subtracted to eliminate, or significantly reduce, the effect of under layers in each measurement result. The use of measurement data associated with multiple targets increases the sample and process information embedded in the model. In particular, the use of training data that includes measurements of multiple, different targets at one or more measurement sites enables more accurate measurements.

In one example, a measurement model is created from spectral measurements of a DOE wafer for both isolated and dense targets. The measurement model is then trained based on the spectral measurement data and known structural parameter values. The resulting trained measurement models are subsequently employed to calculate structural parameter values for both isolated and dense targets on sample wafers. In this manner, each parameter has its own trained model that calculates the parameter value from the measured spectra (or extracted features) associated with both isolated and dense targets.

In another further aspect, measurement data derived from measurements performed by a combination of multiple, different measurement techniques is collected for model building, training, and measurement. The use of measurement data associated with multiple, different measurement techniques increases the sample and process information embedded in the model and enables more accurate measurements. Measurement data may be derived from measurements performed by any combination of multiple, different measurement techniques. In this manner, different measurement sites may be measured by multiple, different measurement techniques to enhance the measurement information available for characterization of the semiconductor structures.

In general, any measurement technique, or combination of two or more measurement techniques may be contemplated within the scope of this patent document. Exemplary measurement techniques include, but are not limited to spectroscopic ellipsometry, including Mueller matrix ellipsometry, spectroscopic reflectometry, spectroscopic scatterometry, scatterometry overlay, beam profile reflectometry, both angle-resolved and polarization-resolved, beam profile ellipsometry, single or multiple discrete wavelength ellipsometry, transmission small angle x-ray scatterometer (TSAXS), small angle x-ray scattering (SAXS), grazing incidence small angle x-ray scattering (GISAXS), wide angle x-ray scattering (WARS), x-ray reflectivity (XRR), x-ray diffraction (XRD), grazing incidence x-ray diffraction (GIXRD), high resolution x-ray diffraction (HRXRD), x-ray photoelectron spectroscopy (XPS), x-ray fluorescence (XRF), grazing incidence x-ray fluorescence (GIXRF), low-energy electron induced x-ray emission scatterometry (LEXES), x-ray tomography, and x-ray ellipsometry. In general, any metrology technique applicable to the characterization of semiconductor structures, including image based metrology techniques, may be contemplated. Additional sensor options include electrical sensors such as non-contact capacitance/voltage or current/voltage sensors which bias the device and detect the resulting bias with an optical sensor (or the converse), or assisted optical techniques, such as XRD, XRF, XPS, LEXES, SAXS, and pump probe techniques. In one embodiment a two-dimensional beam profile reflectometer (pupil imager) may be used to collect both angle resolved and/or multi-spectral data in a small spot size. A UV Linnik interferometer may also be used as a Mueller matrix spectral pupil imager.

In some examples, the model building, training, and measurement methods described herein are implemented as an element of a SpectraShape® optical critical-dimension metrology system available from KLA-Tencor Corporation, Milpitas, Calif., USA. In this manner, the model is created and ready for use immediately after the DOE wafer spectra are collected by the system.

In some other examples, the model building and training methods described herein are implemented off-line, for example, by a computing system implementing AcuShape® software available from KLA-Tencor Corporation, Milpitas, Calif., USA. The resulting, trained model may be incorporated as an element of an AcuShape® library that is accessible by a metrology system performing measurements.

In another example, the methods and systems described herein may be applied to overlay metrology. Grating measurements are particularly relevant to the measurement of overlay. The objective of overlay metrology is to determine shifts between different lithographic exposure steps. Performing overlay metrology on-device is difficult due to the small size of on-device structures, and the typically small overlay value.

For example, the pitch of typical scribe line overlay metrology structures varies from 200 nanometers to 2,000 nanometers. But, the pitch of on-device, overlay metrology structures is typically 100 nanometers or less. In addition, in a nominal production environment, the device overlay is only a small fraction of the periodicity of the device structure. In contrast, proxy metrology structures used in scatterometry overlay are frequently offset at larger values, e.g., quarter of the pitch, to enhance signal sensitivity to overlay.

Under these conditions, overlay metrology is performed with sensor architectures having sufficient sensitivity to small offset, small pitch overlay. The methods and systems described herein may be employed to obtain a measurement signal sensitive to overlay based on on-device structures, proxy structures, or both.

After acquisition, the measured signals are analyzed to determine overlay error based on variations in the measured signals. In one further aspect, the spectral or angle-resolved data is analyzed using PCA, and an overlay model is trained to determine overlay based on the principal components detected in the measured signal. In one example, the overlay model is a neural network model. In this sense, the overlay model is not a parametric model, and thus is not prone to errors introduced by inaccurate modeling assumptions.

In some embodiments, the training of the overlay metrology model is based on measurements of dedicated metrology structures which are nominally identical to the device features but with larger offsets. This can help to overcome the sensitivity problem. These offsets can be introduced by fixed design offsets introduced between features in the two layers to be measured during reticle design. The offsets can also be introduced by shifts in the lithography exposure. The overlay error may be extracted more efficiently from the compressed signal (e.g., PCA signal) by using multiple, shifted targets (e.g., pitch/4 and −pitch/4) and the effect of the underlayer may also be reduced.

In general, the methods and systems for performing semiconductor metrology presented herein may be applied directly to actual device structures or to dedicated metrology targets (e.g., proxy structures) located in-die or within scribe lines.

In yet another aspect, the measurement techniques described herein can be used to provide active feedback to a process tool (e.g., lithography tool, etch tool, deposition tool, etc.). For example, values of the structural parameters determined using the methods described herein can be communicated to a lithography tool to adjust the lithography system to achieve a desired output. In a similar way etch parameters (e.g., etch time, diffusivity, etc.) or deposition parameters (e.g., time, concentration, etc.) may be included in a measurement model to provide active feedback to etch tools or deposition tools, respectively.

In general, the systems and methods described herein can be implemented as part of a dedicated metrology tool, or alternatively implemented as part of a process tool (e.g., lithography tool, etch tool, etc.).

As described herein, the term "critical dimension" includes any critical dimension of a structure (e.g., bottom critical dimension, middle critical dimension, top critical dimension, sidewall angle, grating height, etc.), a critical dimension between any two or more structures (e.g., distance between two structures), and a displacement between two or more structures (e.g., overlay displacement between overlaying grating structures, etc.). Structures may include three dimensional structures, patterned structures, overlay structures, etc.

As described herein, the term "critical dimension application" or "critical dimension measurement application" includes any critical dimension measurement.

As described herein, the term "metrology system" includes any system employed at least in part to characterize a specimen in any aspect, including measurement applications such as critical dimension metrology, overlay metrology, focus/dosage metrology, and composition metrology. However, such terms of art do not limit the scope of the term "metrology system" as described herein. In addition, the metrology system 400 may be configured for measurement of patterned wafers and/or unpatterned wafers. The metrology system may be configured as a LED inspection tool, edge inspection tool, backside inspection tool, macro-inspection tool, or multi-mode inspection tool (involving data from one or more platforms simultaneously), and any other metrology or inspection tool that benefits from the calibration of system parameters based on critical dimension data.

Various embodiments are described herein for a semiconductor processing system (e.g., an inspection system or a lithography system) that may be used for processing a specimen. The term "specimen" is used herein to refer to a wafer, a reticle, or any other sample that may be processed (e.g., printed or inspected for defects) by means known in the art.

As used herein, the term "wafer" generally refers to substrates formed of a semiconductor or non-semiconductor material. Examples include, but are not limited to, monocrystalline silicon, gallium arsenide, and indium phosphide. Such substrates may be commonly found and/or processed in semiconductor fabrication facilities. In some cases, a wafer may include only the substrate (i.e., bare wafer). Alternatively, a wafer may include one or more layers of different materials formed upon a substrate. One or more layers formed on a wafer may be "patterned" or "unpatterned." For example, a wafer may include a plurality of dies having repeatable pattern features.

A "reticle" may be a reticle at any stage of a reticle fabrication process, or a completed reticle that may or may not be released for use in a semiconductor fabrication facility. A reticle, or a "mask," is generally defined as a substantially transparent substrate having substantially opaque regions formed thereon and configured in a pattern. The substrate may include, for example, a glass material such as amorphous $SiO_2$. A reticle may be disposed above a resist-covered wafer during an exposure step of a lithography process such that the pattern on the reticle may be transferred to the resist.

One or more layers formed on a wafer may be patterned or unpatterned. For example, a wafer may include a plurality of dies, each having repeatable pattern features. Formation and processing of such layers of material may ultimately result in completed devices. Many different types of devices may be formed on a wafer, and the term wafer as used herein is intended to encompass a wafer on which any type of device known in the art is being fabricated.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

Although certain specific embodiments are described above for instructional purposes, the teachings of this patent document have general applicability and are not limited to the specific embodiments described above. Accordingly, various modifications, adaptations, and combinations of various features of the described embodiments can be practiced without departing from the scope of the invention as set forth in the claims.

What is claimed is:

1. A metrology system comprising:
   an illumination subsystem that provides an amount of illumination light to one or more metrology targets disposed on a wafer previously processed by a plurality of process steps of a fabrication process flow;
   a detector subsystem that detects an amount of light from the one or more metrology targets in response to the amount of illumination light and generates an amount of measurement signals in response to the amount of detected light; and a computing system configured to:
receive a first amount of process information from a first process tool employed to execute a first process step of the plurality of process steps on the wafer;
receive a second amount of process information from the first process tool or another process tool employed to execute a second process step of the plurality of process steps on the wafer; and
estimate a value of a structural parameter of interest of the one or more metrology targets based on the amount of measurement signals and the first and second amounts of process information.

2. The metrology system of claim 1, wherein the computing system is further configured to:
estimate a value of a correctable parameter associated with at least one of the process steps based on the measured characteristic of the metrology target and the first and second amounts of process information; and
communicate the value of the correctable parameter to at least one process tool employed to execute the at least one process step.

3. The metrology system of claim 1, wherein the first amount of process information includes any of a process control parameter, a process tool set-up parameter, a process environment parameter, an amount of process data collected from sensors on board the first process tool, and an amount of metrology data collected from sensors on board the first process tool.

4. The metrology system of claim 1, wherein the first amount of process information includes a lithography focus parameter value, a lithography dosage parameter value, or a combination thereof.

5. The metrology system of claim 1, wherein the estimating the value of the parameter of interest of the one or more metrology targets involves a physical model or a trained input-output measurement model.

6. The metrology system of claim 5, wherein the computing system is further configured to:
train the input-output measurement model with simulated measurement data and simulated process information, actual measurement data and process information associated with a Design of Experiments (DOE) wafer, or a combination thereof.

7. The metrology system of claim 1, wherein the computing system is further configured to:
reduce a dimension of the first and second amounts of process information, the amount of measurement signals, or a combination thereof.

8. The metrology system of claim 1, wherein the detector is configured to collect light from the target structure at multiple wavelengths, multiple collection angles, or a combination of multiple wavelengths and multiple collection angles.

9. A metrology system comprising:
an illumination subsystem that provides an amount of illumination light to one or more metrology targets disposed on a wafer previously processed by a plurality of process steps of a fabrication process flow;
a detector subsystem that detects an amount of light from the one or more metrology targets in response to the amount of illumination light and generates an amount of measurement signals in response to the amount of detected light; and
a non-transitory, computer-readable medium, comprising:
code for causing a computer system to receive a first amount of process information from a first process tool employed to execute a first process step of the plurality of process steps on the wafer;
code for causing the computer system to receive a second amount of process information from the first process tool or another process tool employed to execute a second process step of the plurality of process steps on the wafer; and
code for causing the computer system to estimate a value of a structural parameter of interest of the one or more metrology targets based on the amount of measurement signals and the first and second amounts of process information.

10. The metrology system of claim 9, the non-transitory, computer-readable medium, further comprising:
code for causing the computer system to estimate a value of a correctable parameter associated with at least one of the process steps based on the measured characteristic of the metrology target and the first and second amounts of process information; and
code for causing the computer system to communicate the value of the correctable parameter to at least one process tool employed to execute the at least one process step.

11. A method comprising:
receiving a wafer including one or more metrology targets fabricated by a plurality of process steps of a fabrication process flow executed by a plurality of process tools;
receiving a first amount of process information from a first process tool employed to execute a first process step of the plurality of process steps on the wafer;
receiving a second amount of process information from the first process tool or another process tool employed to execute a second process step of the plurality of process steps on the wafer;
providing an amount of illumination light to the one or more metrology targets;
detecting an amount of light from the one or more metrology targets in response to the illumination;
generating an amount of measurement signals in response to the amount of detected light;
estimating a value of a parameter of interest of the one or more metrology targets based on the amount of measurement signals and the first and second amounts of process information.

12. The method of claim 11, further comprising:
estimating a value of a correctable parameter associated with at least one of the process steps based on the measured characteristic of the metrology target and the first and second amounts of process information; and
communicating the value of the correctable parameter to at least one process tool employed to execute the at least one process step.

13. The method of claim 11, wherein the plurality of process tools involved in the fabrication process flow includes at least one lithography tool and at least one etch tool.

14. The method of claim 11, wherein any of the first and second amounts of process information includes a process parameter value.

15. The method of claim 14, wherein the process parameter value is any of a lithography focus parameter value, a lithography dosage parameter value, or a combination thereof.

16. The method of claim 11, wherein any of the first and second amounts of process information includes a characteristic of the metrology target measured by a metrology system on-board the first process tool.

17. The method of claim 11, wherein the estimating the value of the parameter of interest of the one or more metrology targets involves a physical model or a trained input-output measurement model.

18. The method of claim 17, further comprising:
training the input-output measurement model with simulated measurement data and simulated process information, actual measurement data and process information associated with a Design of Experiments (DOE) wafer, or a combination thereof.

19. The method of claim 11, further comprising:
reducing a dimension of the first and second amounts of process information, the amount of measurement signals, or a combination thereof.

20. The method of claim 11, wherein the one or more metrology targets includes a nominal metrology target and at least one assist metrology target, wherein both the nominal metrology target and the at least one assist metrology target are each characterized by at least one parameter of interest generated by at least two patterning steps of a multiple patterning process.

* * * * *